(12) United States Patent
Schaffner

(10) Patent No.: US 7,987,053 B2
(45) Date of Patent: Jul. 26, 2011

(54) MONITOR UNITS CALCULATION METHOD FOR PROTON FIELDS

(75) Inventor: Barbara Ursula Schaffner, Otelfingen (CH)

(73) Assignee: Varian Medical Systems International AG, Postfach (CH)

( * ) Notice: Subject to any disclaimer, the term of this patent is extended or adjusted under 35 U.S.C. 154(b) by 367 days.

(21) Appl. No.: 12/130,770

(22) Filed: May 30, 2008

(65) Prior Publication Data
US 2009/0299634 A1   Dec. 3, 2009

(51) Int. Cl.
*G01F 19/00*   (2006.01)
(52) U.S. Cl. .............. 702/1; 702/179; 702/189
(58) Field of Classification Search .......... 702/1, 179, 702/189; 382/128; 250/281, 286, 289; 128/922
See application file for complete search history.

(56) References Cited

U.S. PATENT DOCUMENTS
4,849,248 A * 7/1989 Hashimoto .............. 427/527
2003/0236646 A1 * 12/2003 Suzuki ..................... 702/179

OTHER PUBLICATIONS

Best Medical Canada, 'Depth Dose Measurements using MOSFETS, diodes and ion chambers', 2000, Technical Note, pp. 1-4.*
Price, 'Calculating percent depth dose with the electron pencil beam redefinition algorithm', 2007, pp. 61-75.*
Levin et al., 'Proton Beam Therapy, 2006-2007, pp. 106-117.*
Kooy et al. "Monitor Unit Calculations for Range-Modulated Spread-out Bragg Peak Fields". Phys. Med. Biol. 48 2797-2808. 2003.
Kooy et al. "The Prediction of Output Factors for Spread-out Proton Bragg Peak Fields in Clinical Practice". Phys. Med. Biol. 48 2797-2808. 2005.

* cited by examiner

*Primary Examiner* — Mohamed Charioui
*Assistant Examiner* — Elias Desta
(74) *Attorney, Agent, or Firm* — Vista IP Law Group, LLP.

(57) ABSTRACT

A method for determining a monitor unit that is associated with a process using ions, includes obtaining a depth dose curve, determining a characteristic parameter based on the depth dose curve, and using the characteristic parameter to determine a first monitor unit factor. A system for determining a monitor unit that is associated with a process using protons, includes a processor that is configured for obtaining a depth dose curve, determining a characteristic parameter based on the depth dose curve, and using the characteristic parameter to determine a first monitor unit factor.

38 Claims, 13 Drawing Sheets

MONITOR UNITS CALCULATION METHOD FOR PROTON FIELDS

FIELD

This invention relates generally to proton therapy, and more specifically, to systems and methods for determining monitor units in proton or ion beam treatment.

BACKGROUND

Radiation therapy has been employed to treat tumorous tissue. In radiation therapy, a high energy beam is applied from an external source towards the patient. The external source produces a collimated beam of radiation that is directed into the patient to the target site. The dose and placement of the dose must be accurately controlled to ensure that the tumor receives sufficient radiation, and that damage to the surrounding healthy tissue is minimized.

Existing radiotherapy systems use electrons to generate the radiation beam. In such systems, the ability to control the dose placement is limited by the physics of the beam, which necessarily irradiates healthy tissue on the near-side and far-side of a target region as it passes through the patient. Thus, it may be desirable to use protons as the source of the radiation. By controlling the energy of the protons, the protons will stop at a precise location within the patient. In this way, tissue on the far-side of the target region does not receive any radiation dose. Further, because the dose provided by a proton is concentrated at a "Bragg peak" around the area where the proton stops, the dose to healthy tissue on the near-side of the target region may also be reduced.

In proton therapy, monitor unit(s) (MU) is a measure of dose, or an amount of radiation units produced by a machine. MU may be determined during treatment planning for planning purpose, and/or during actual treatment for verification of delivery of dose. Previously, in order to calculate monitor units, it was necessary to measure the output for each field before applying it for a patient treatment. A first approach to the calculation of monitor units was published in "Monitor unit calculations for range-modulated spread-out Bragg peak fields" Phys. Med. Biol. 48 2797-2808 by Kooy et al., 2003, and in "The prediction of output factors for spread-out proton Bragg peak fields in clinical practice" Phys. Med. Biol. 50 5847-5856 by Kooy et al., 2005.

Kooy's method has several disadvantages. First, the method is based on a theoretical model of a modulated proton spread-out Bragg peak (SOBP). It is therefore limited to MU calculation for flat SOBPs. Furthermore, it uses some fiddling factors, which must be obtained from a large collection of measurements. These fiddling factors depend on the details of the beamline design of each machine and on different settings of the same beamline design. Also, another method that has been employed for calculating MU may lead to large errors for lower ranges of the beam. These errors are related to a change of the entrance dose with respect to the height of the Bragg peak when changing the amount of absorber material in the beamline. In particular, the gradient in depth dose distribution is increasing with depth (or decreasing with residual range of the beam between its entry point and the Bragg peak). However, it only starts to play a major role at residual ranges below about 15 cm. The effect of this gradient in the depth dose on the MU factor is not addressed before, thereby leading to errors in the calculated MU for lower ranges of the beam. Also, there is some range shift in-between the monitor chamber and isocenter due to air or other materials, which was not considered before. For example, a range shift between the monitor and isocenter of 2-3 mm may contribute to 10% error in the calculated MU for a residual range of 2 cm.

For the foregoing reasons, it would be desirable to have systems and methods for determining monitor units that does not require a lot of calibration measurements to find machine specific factors. It would also be desirable to have systems and methods for determining monitor units that are more accurate for lower (residual) ranges of energy.

SUMMARY

In accordance with some embodiments, a method for determining a monitor unit that is associated with a process using ions, includes obtaining a depth dose curve, determining a characteristic parameter based on the depth dose curve, and using the characteristic parameter to determine a first monitor unit factor. In some embodiments one or more correction factors may be applied to the first monitor unit factor.

In accordance with other embodiments, a system for determining a monitor unit that is associated with a process using ions, includes a processor that is configured for obtaining a depth dose curve, determining a characteristic parameter based on the depth dose curve, and using the characteristic parameter to determine a first monitor unit factor. In some embodiments one or more correction factors may be applied to the first monitor unit factor.

In accordance with other embodiments, a computer product includes a set of instructions, an execution of which causes a process to be performed, wherein the process is for determining a monitor unit that is associated with a process using ions, the process comprising obtaining a depth dose curve, determining a characteristic parameter based on the depth dose curve, and using the characteristic parameter to determine a first monitor unit factor. In some embodiments one or more correction factors may be applied to the first monitor unit factor.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
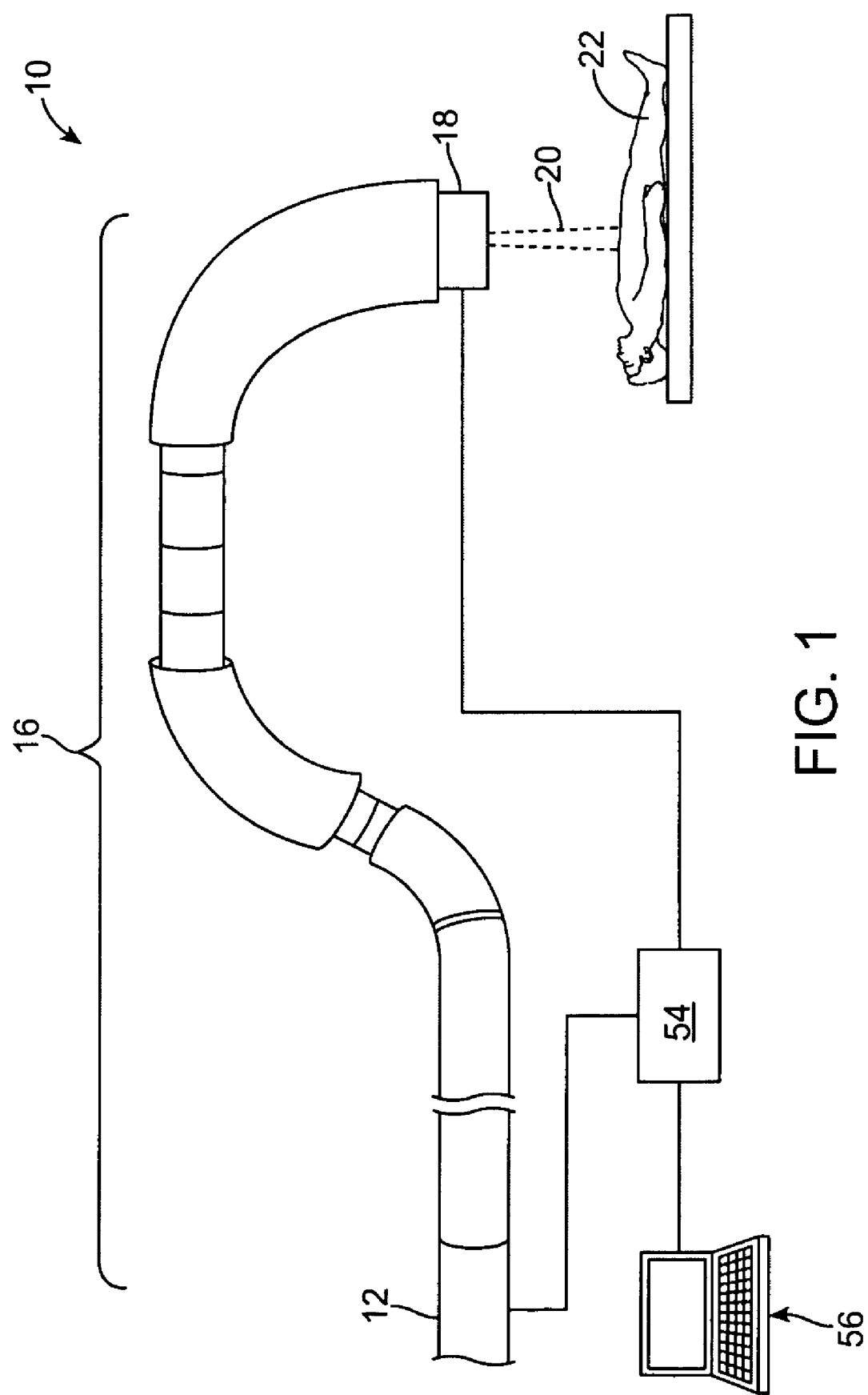
FIG. 1 is a block diagram of a proton system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Referring now to the drawings, in which similar or corresponding parts are identified with the same reference numeral, FIG. 1 illustrates a proton system 10, in accordance with some embodiments. The proton system 10 includes a proton generator 12, a beam transport system 16, and a nozzle 18. The proton generator 12 is for providing accelerated protons, which may be decelerated by the beam transport system 16. The beam transport system 16 also includes a plurality of magnets for steering the proton beam to a desired location, e.g., a particular treatment room. The accelerator may be a cyclotron, which provides a fixed energy, or alternatively, a synchrotron, which provides variable energy. Typically, the beam transport system 16 may be used for guiding the beam to more than one treatment rooms. The nozzle 18 is mounted on a gantry (e.g., a rotatable gantry) or a fixed beam port. The nozzle 18 is for adjusting the proton beam so that the beam 20 has a certain desired characteristic for treating a patient 22.

The system 10 also includes a processor 54, which may be used to control an operation of the proton source 12, and/or an operation of the nozzle 18. In some cases, the processor 54 may also be used to obtain data regarding an operation of the proton machine, perform analysis and calculation on dose, and other functions, such as those described herein. The system 10 may also include an user interface 56 having a monitor and an input device (e.g., keyboard, mouse, etc.) for allowing a user to input and receive data.

Figure 2:
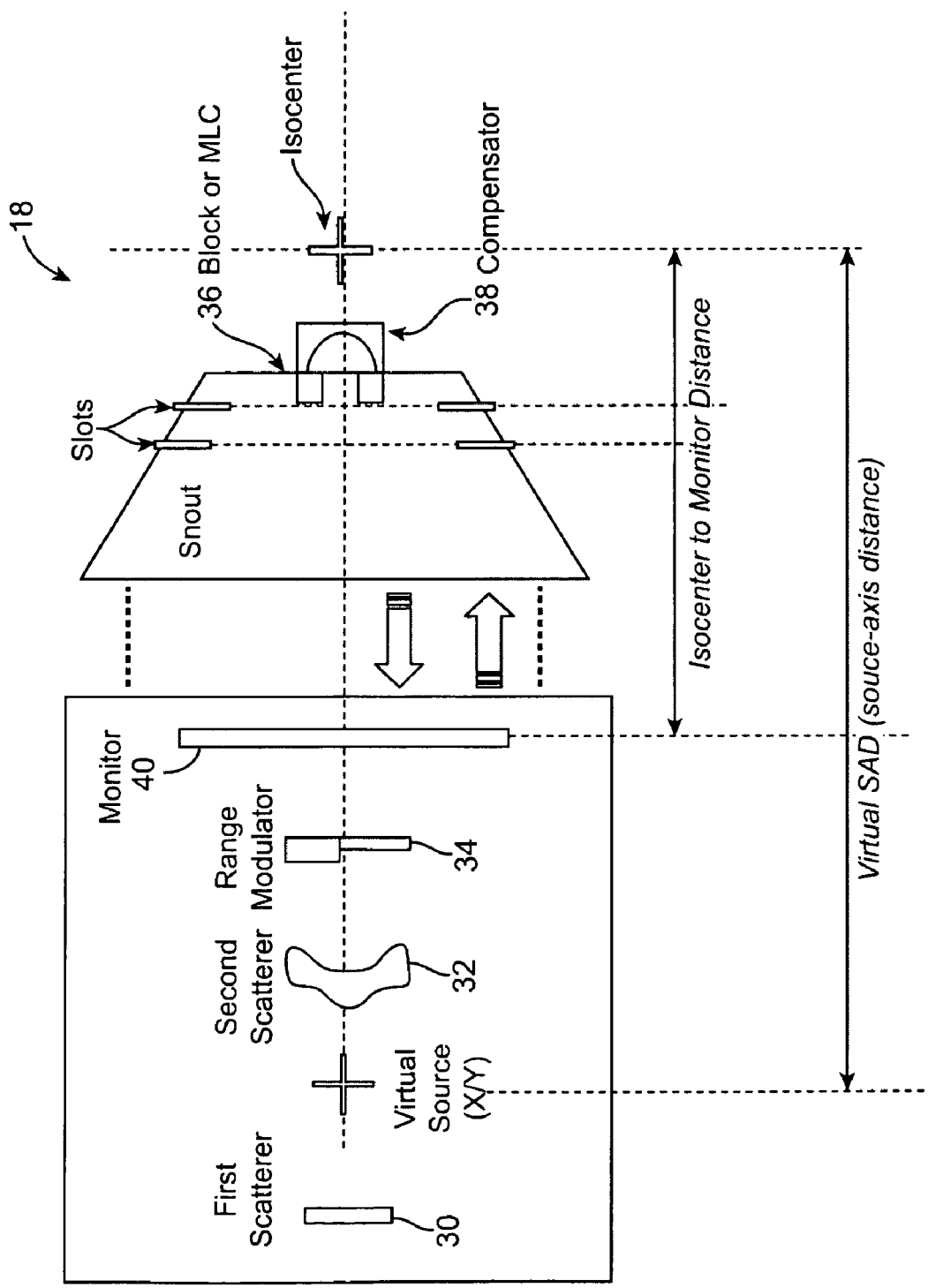
FIG. 2 is a schematic diagram of a nozzle in accordance with some embodiments.

FIG. 2 illustrates the nozzle 18 of the system 10 in accordance with some embodiments. The nozzle 18 may include a first scatterer 30, a second scatterer 32, a range modulator 34, a block or collimator 36, a compensator 38, and a monitor 40. It could also include other beam steering and shaping devices, e.g. deflecting magnets (not shown). The second scatterer 32 is upstream from the range modulator 34. In other embodiments, the second scatterer 32 may be downstream from the range modulator 34. Also, in other embodiments, the relative positions between the various components may be different from those illustrated in the figure. As shown in FIG. 2, the source axis distance (SAD) is the distance between the proton source (virtual source) and the isocenter. The position of the proton source may change between different procedure techniques and beam-line settings. The virtual source is obtained from measurements of the increase of the field size with distance along the beam axis. It lies somewhere between the first and second scatterers 30, 32.

Figure 3:
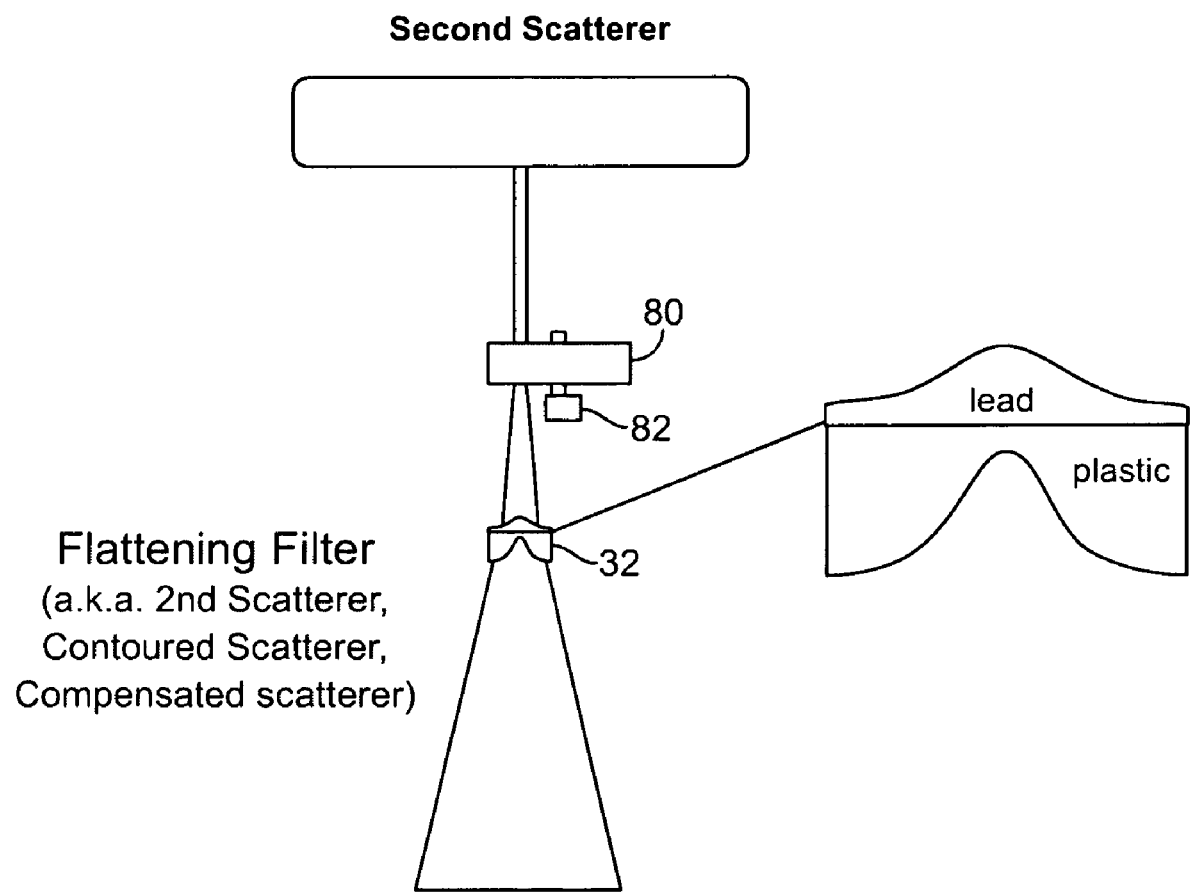
FIG. 3 illustrates a scatterer.

With reference to FIGS. 2 and 3, the first scatterer 30 is for scattering the beam to thereby obtain a Gaussian shaped transversal distribution (cross fluence). The second scatterer 32 is for further scattering the beam more along the central axis and less on the sides. Thus, a broad field of uniform fluence distribution is obtained. In some cases, non-uniform cross profiles (e.g. single scattering technique, where the second scatterer is left out) may also be used. This second scatterer 32 has a similar function as the flattening filter in a proton machine. The second scatterer 32 comprises a contoured scatterer, and has a shape such as that shown in FIGS. 2 and 3. The second scatterer 32 has side portions that are thicker than its middle portion. In the illustrated embodiments, the second scatterer 32 has a top portion that is made from lead, and a bottom portion that is made from plastic. The top portion may be a high scattering material in order to distribute the number of protons evenly across the whole field. The bottom portion ensures that the energy of all protons remains substantially equal after the second scatterer. Without the bottom portion, the protons which are scattered in the center of the lead would have a lower energy than the protons which are passed further away from the central axis. In other embodiments, the second scatterer 32 may have different shapes, may be made from other materials, or it may not be present at all (e.g., for small fields).

Figure 4:
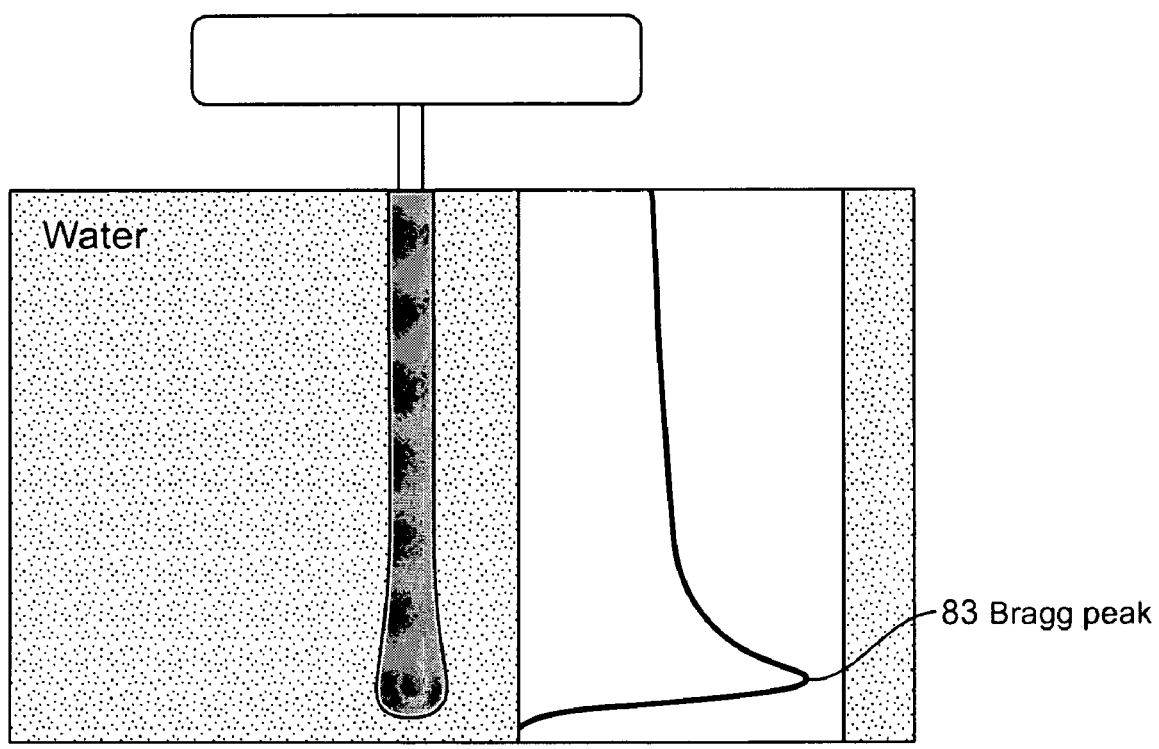
FIG. 4 illustrates a single Bragg peak curve.
Figure 5:
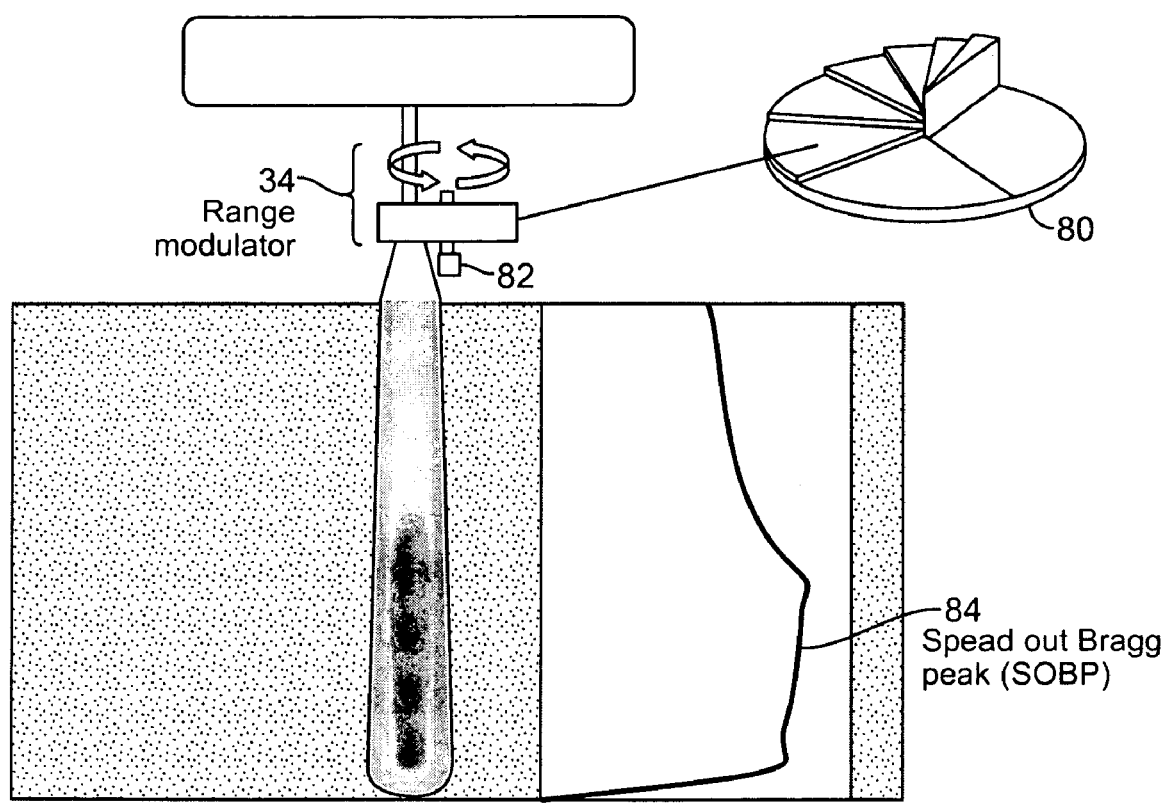
FIG. 5 illustrates a range modulator creating a spread out Bragg peak curve.

When a proton beam is delivered into water, it results in a single Bragg peak curve 83, such as that shown in FIG. 4. As illustrated by the Bragg peak curve 83, the energy is concentrated at a location at which the beam ends. The range modulator 34 is configured to spread such concentration of energy. The range modulator 34 includes a disk 50 and a positioner 52 for rotating the disk 50 (FIG. 5). The disk 80 has a step configuration such that different portions of the disk 80 have different respective thicknesses. During use, the positioner 82 places different portions of the disk 80 in front of the beam such that the beam is filtered by different portions of the disk 80 that have different thicknesses. The thicker portions reduce the energy of the proton beam more than the relatively thinner portions. As a result, the range modulator 34 adjusts the beam such that the beam has a spread out Bragg peak (SOBP) 84.

Figure 6:
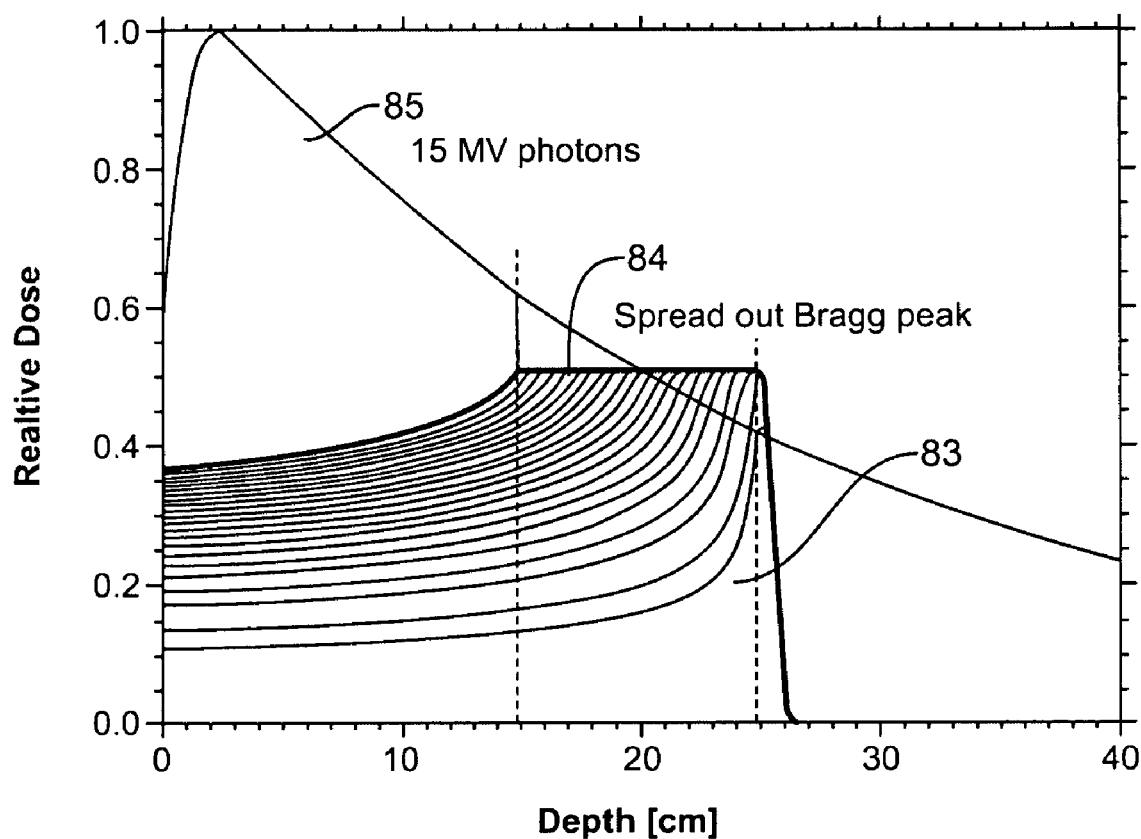
FIG. 6 illustrates a single Bragg peak curve and a spread out Bragg peak curve.

FIG. 6 illustrates the single Bragg peak curve 83 and the SOBP 84. The single Bragg peak curve 83 is a depth dose distribution of a near-monoenergetic or pristine beam of protons. The SOBP 84 is a depth dose distribution created by summing up a set of appropriately weighted Bragg peaks. A SOBP features an approximately uniform high dose region with a steep dose that falls off distally, and a lower dose lower than the high dose proximally. The SOBP 84 is obtained by combining energies from different layers, which are associated with the different thicknesses of the range modulator 34. Each layer may have a value (e.g., a nozzle equivalent thickness NeT) that represents a scattering feature (or a total amount of absorbing material along the beam-line) associated with that layer, wherein the scattering feature may be due to the range modulator 34, scatterers 30, 32, and air. In some embodiments, the NeT term has a component which is constant for all layers (scatterers, air, etc.) and a variable component (e.g., due to different disk thicknesses of the range modulator 34). Curve 85 is a depth dose curve of a beam as produced by a conventional LINAC—shown for comparison to illustrate the advantages of protons.

Figure 7:
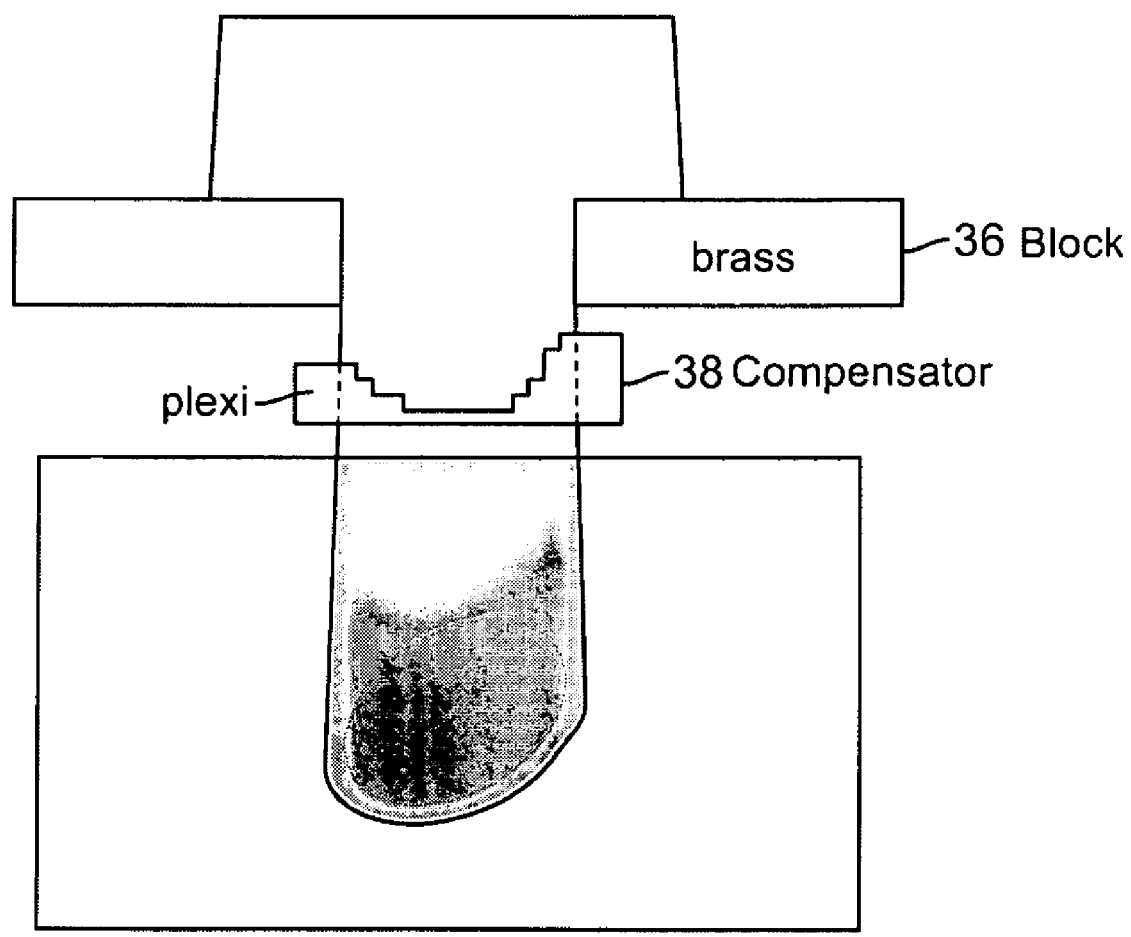
FIG. 7 illustrates a collimator and a compensator.

With reference to FIG. 7, the collimator 36 is for blocking at least some of the beam so that the resulting beam conforms to a shape of a target region. In the illustrated embodiments, the collimator 36 comprises a multi-leaf collimator, and includes a plurality of leafs or fingers that are slidable relative to each other. During use, the leafs are positioned to thereby form a desired shape of an opening for allowing the beam to pass through the collimator 36. In other embodiments, the collimator 36 may be a single block having an opening that is predetermined. The collimator 36 may be made from brass or other materials.

The compensator 38 is for further adjusting the beam such that different portions of the beam penetrate at different depths at a target region. In the illustrated embodiments, the compensator 38 has a contour that is determined in accordance to the shape of the target region, and it varies from patient to patient (i.e., patient-specific). The compensator 38 may be made from a plastic material, such as polyethylene or Lucite (aka plexi, perspex), or other materials. In some embodiments, the collimator 36 and the compensator 38 may be detachably coupled to a snout. During use, the snout can be moved along the beam axis in order to bring the collimator 36 and the compensator 38 as close to the patient 22 as possible.

Figure 8:
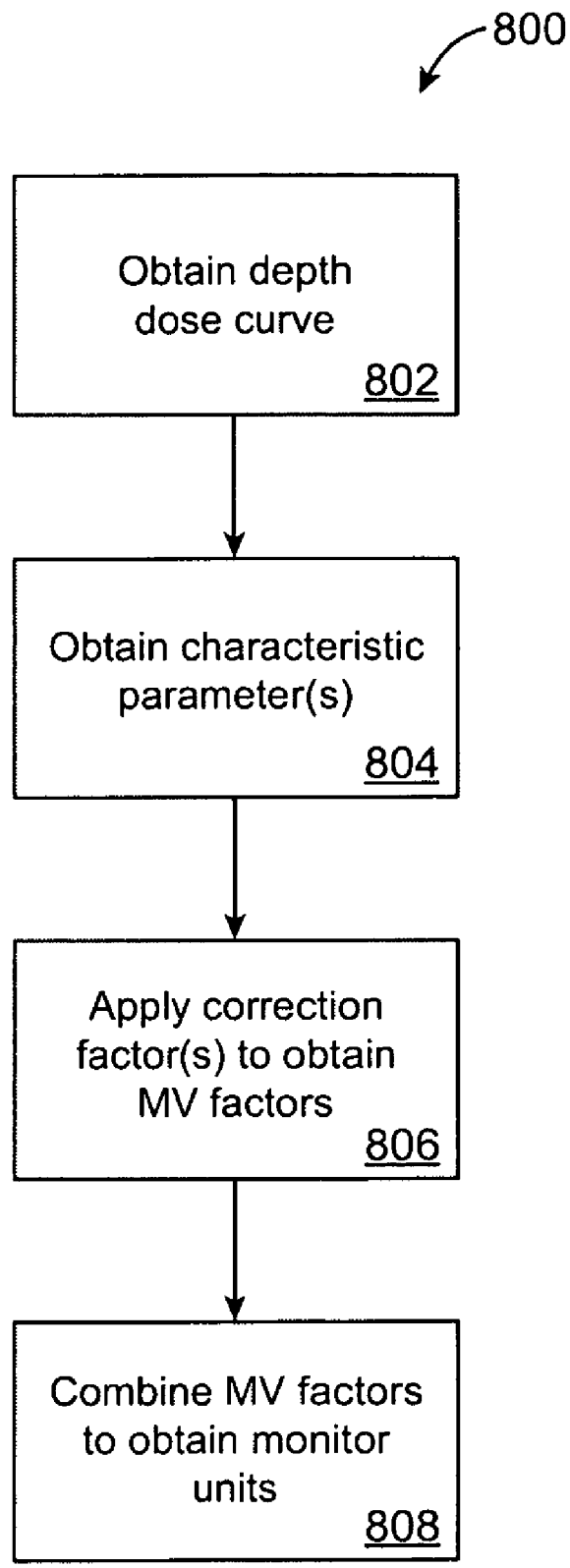
FIG. 8 illustrates a method for determining a monitor unit in accordance with some embodiments.

A method 800 for calculating monitor units (MU) for SOBP fields (or non-homogeneous spread-out Bragg peaks) in accordance with some embodiments will now be described with reference to FIG. 8. As used in this specification, the terms "monitor unit" and "monitor units" are synonymous, and may refer to one or more measure of radiation dose. The scale of the monitor unit can be defined arbitrarily, as long as it is proportional to the dose in the patient.

In the illustrated embodiments, the method uses measurements of non-shifted Bragg peaks in absolute units (Gy/MU) and a relative change of the fluence at isocenter with passive range changes (i.e., by means of absorber material in the beam-line). In particular, one depth dose is measured per energy at nozzle entrance, wherein each energy corresponds to a respective field. Also, in the illustrated embodiments, the MU calculation involves use of the following input: (1) measured depth dose curve for a pristine Bragg peak(s) with information about the nominal energy of the beam (i.e., at nozzle entrance) and the total amount of range absorbing material in the beam-line (NeT), (2) distance between the monitor chamber and isocenter, (3) estimate of the range shift between the monitor chamber and isocenter (typically only for higher order corrections), (4) source-axis-distance (SAD) for each pristine Bragg peak, (5) relative measurement of the fluence at isocenter as a function of an NeT variation, and (6) analytical model of the depth dose curve. In other embodiments, one or more of these input may be omitted, depending on the complexity of the beam-line design and the level of accuracy required for a particular application.

Figure 9A:
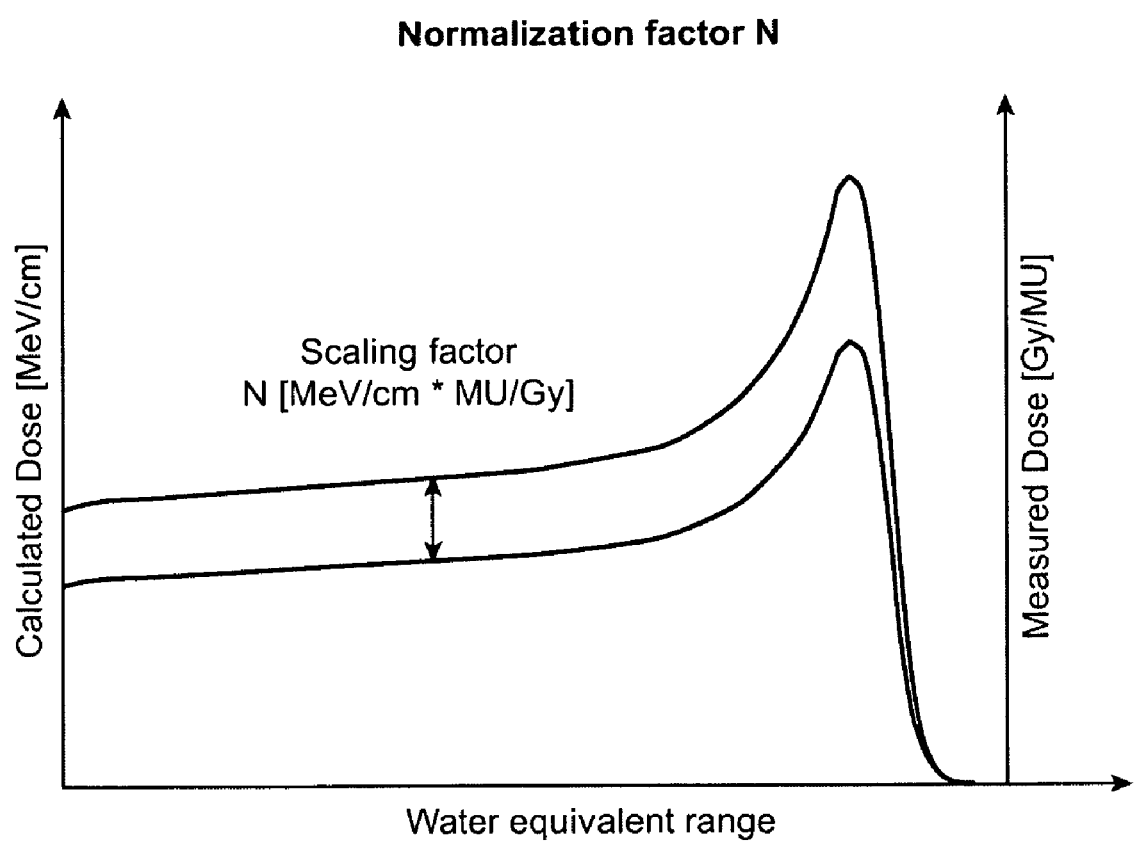
FIG. 9A illustrates a concept of a normalization factor.

First, a depth dose curve is obtained (Step 802). This may be accomplished by shooting a beam into water to obtain a measurement. Next, an analytical model is fitted to the depth dose curve and characteristic parameter(s) is extracted (Step 804). An analytical model may be expressed as a formula with variables. The fitting of the analytical model may be accomplished by determining the variables (parameters) of the formula such that it best matches the measured data of the depth dose curve. In the illustrated embodiments, a characteristic parameter may be a normalization factor, which is used in the analytical model to convert the unit of the dose in the analytical model (MeV/cm) into Gy/MU. The normalization factor N relates the measured dose in the water phantom with the (measured) monitor signal and the theoretical depth dose model (See FIG. 9A showing an upper curve representing calculated dose as a function of water equivalent range, a lower curve representing measured dose as a function of water equivalent range, and normalization factor N that is determined by dividing calculated dose by the measured dose). The monitor signal, which may be a measured of a current, is proportional to the monitor units. A certain amount of current is defined to be 1 MU. In some embodiments, certain assumptions may be made in the model. For example, N (ratio between monitor signal and measured dose) may be assumed to remain constant as a function of the monitor units (intensity of the beam). Since N increases with the monitor signal and decreases with the measure dose, if the monitor signal increases, the dose would increase correspondingly according to such assumption. It should be noted that the use of the analytical depth dose model is not required for MU calculation, and that in other embodiments, measured curves may be used directly, provided that they can be measured up to the surface of the patient 22.

Other characteristic parameters (such as the apparent energy, the energy (or range) spread, the number of scattered particles leaving the beamline) for the analytical depth dose model may also be determined from the measured depth dose. It is desirable that the characteristic parameters be those that do not depend on the NeT. In such cases, the NeT dependence of the measured curve may be removed by shifting the whole curve in depth by the NeT value. If the depth dose was measured in a divergent geometry (scattering technique), a divergence correction must first be applied by using the SAD information and the distance between isocenter and monitor. In the scattering technique, the beam is scattered in order to produce a larger field from a small beam. The divergence correction is for correcting for the loss of beam intensity as the beam spreads over a larger area, which is well known in the art. The divergence correction is not needed, if the beam is measured without any spreading devices in the beamline.

Next, correction factor(s) are applied to the normalization factor N to obtain MU factors (Step 806). In the illustrated embodiments, the MU factors for different respective layers of the SOBP are determined by the following equation:

$$MU \text{ factor}(NeT_i) = N(NeT_R) \cdot \frac{D^{in}(NeT_i)}{D^{in}(NeT_R)},$$

$$\frac{\Phi(NeT_R)}{\Phi(NeT_i)} \cdot \frac{\frac{D^{in}(NeT_R)}{D^{in}(NeT_R + IsoMonWeT)}}{\frac{D^{in}(NeT_i)}{D^{in}(NeT_i + IsoMonWeT)}}$$

where:
N is the normalization factor extracted from the measured depth dose curve for the reference $NeT_R$,
$NeT_R$ is the reference nozzle equivalent thickness (which is the total nozzle equivalent thickness for the measured Bragg peak minus the range shift between monitor chamber and isocenter),
$NeT_i$ is the nozzle equivalent thickness for beam-line setting of layer i up to the monitor chamber,
$D^{in}$ is entrance dose (or dose at monitor chamber) for the given NeT, and
$\phi$ is fluence at isocenter for the given NeT.

The first term $N(NeT_R)$ is the normalization factor that corresponds to $NeT_R$, which is obtained from step 804. The reference $NeT_R$ is the NeT at which the depth dose is measured minus the range shift between monitor chamber and isocenter. In some embodiments, it may be the deepest possible layer for the given energy. In such cases, it is measured with the minimal thickness of the range modulator 34. In other embodiments, the reference $NeT_R$ may be associated with other layers that may not be the deepest possible layer.

Figure 9B:
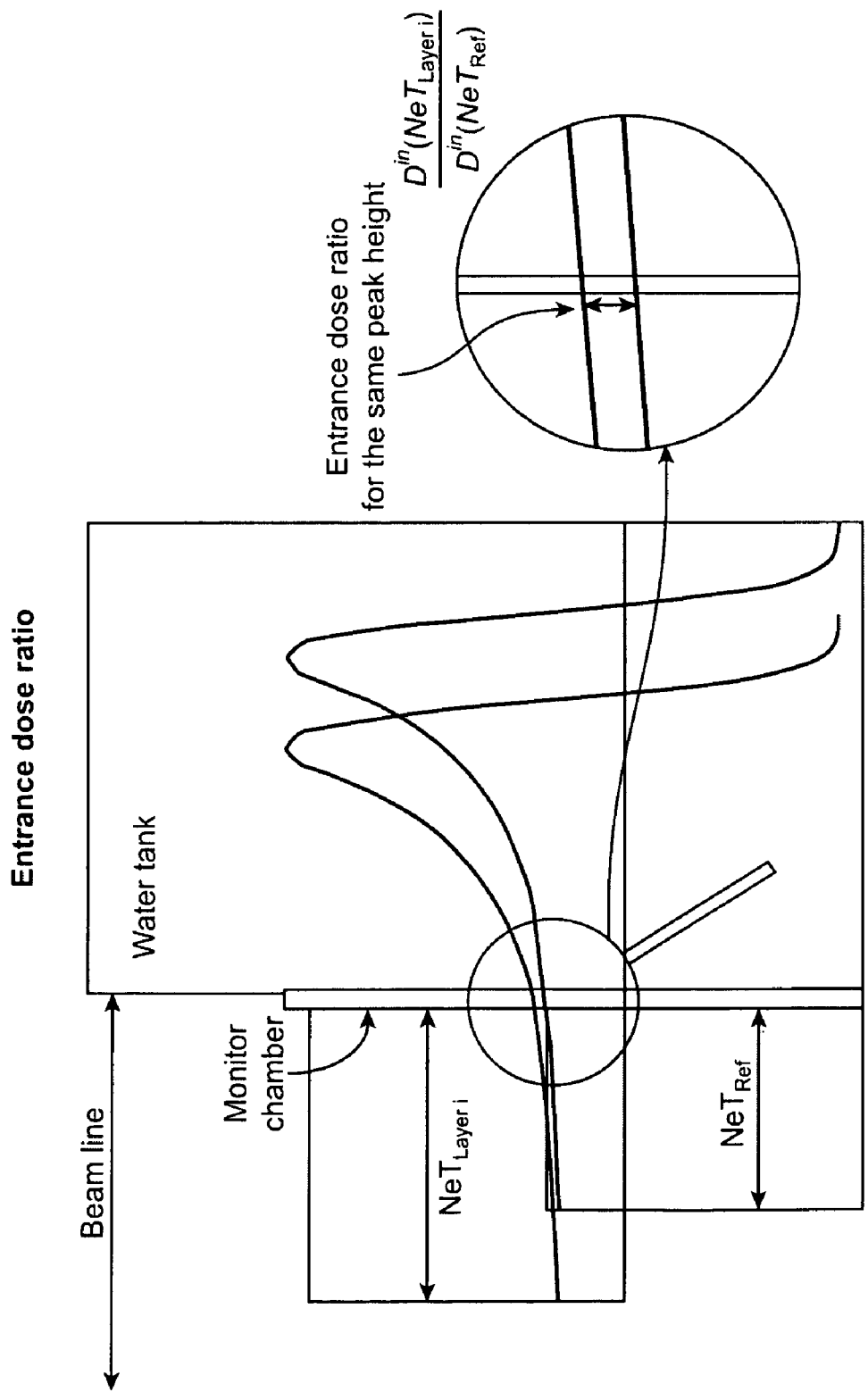
FIGS. 9B-9D illustrate examples of correction factors that may be applied to a normalization factor.

The second term $D^{in}(NeT_i)/D^{in}(NeT_R)$ in the above equation represents the ratio between the expected entrance dose for layer i and the entrance dose for the reference layer, and is used to adjust the N value to account for the difference in the depth dose curve between the two NeT shifts, or in other words for the difference in peak to entrance ratio (See FIG. 9B). Various techniques may be used to determine the entrance dose D. In the illustrated embodiments, the method uses a theoretical model (which may be, for example, a formula in which D is a variable) of the depth dose curve to obtain the dose at all positions (calculated in MeV/cm per proton).

Figure 9C:
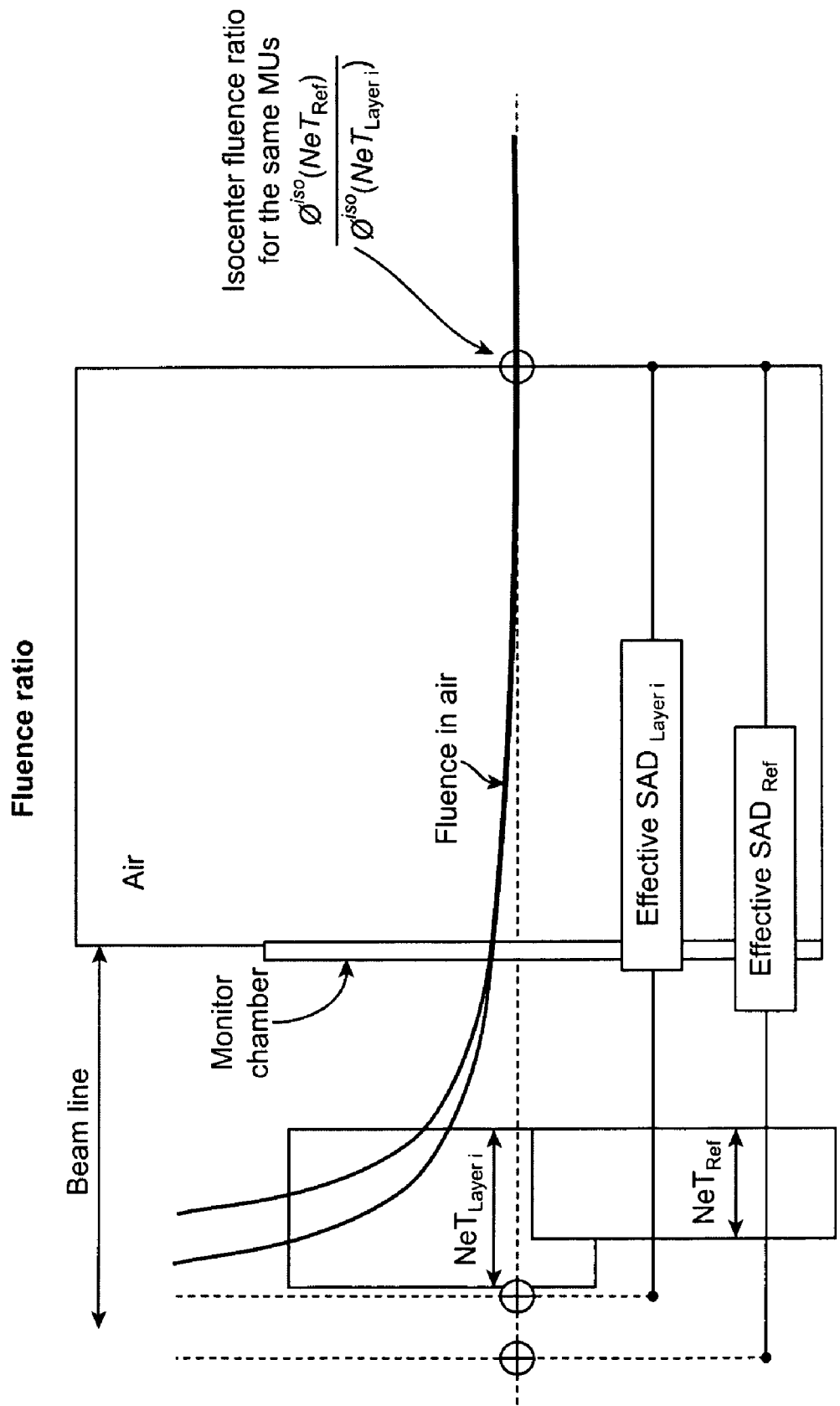

The third term $\phi(NeT_R)/\phi(NeT_i)$ in the above equation represents the ratio between the fluence under reference condition and the fluence for the actual layer i, and is used to adjust the N value to account for the change in fluence (beam intensity) between the layer R and layer I (See FIG. 9C). In some embodiments, one can measure depth dose curves for all layers and extract the factor N for each of the layers. However, such measurements may be time consuming. Therefore, the factor N is corrected for the shallower layers with the ratio of fluences (one measurement point per energy/NeT combination). The fluence $\phi$ at isocenter for the given NeT may be taken from measurements (i.e., the dose in air at isocenter is measured for a fixed number of MUs for each layer). In other embodiments it may be estimated from previous knowledge of the effective SAD for the particular beamline configuration. Note that in the above equation, the ratio between two measurements is used in the correction factor. It is therefore not sensitive to the method of measuring the fluence or to possible backscatter correction factors.

Figure 9D:
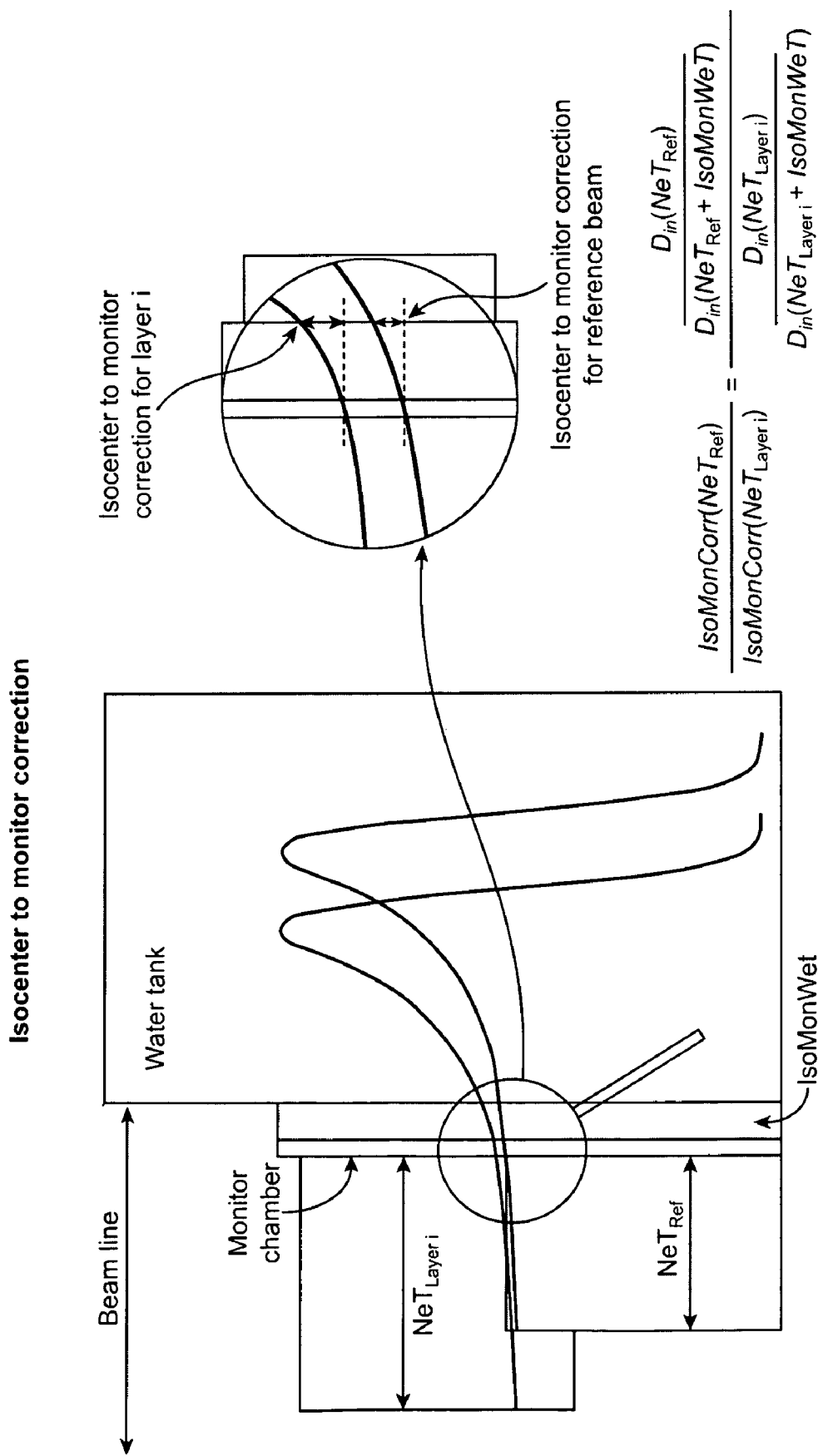

The last term in the above equation represents a higher order correction to take the depth dose change between the monitor chamber and isocenter into account, and is a correction for the ratio of values of the entrance dose at the monitor position and at isocenter (See FIG. 9D). The isocenter to monitor correction factor $D(NeT)/D(NeT+IsoMonWeT)$ accounts for the fact that the dose measured in the monitor chamber may not be exactly equal to the dose at the patient surface. The ratio of isocenter to monitor correction factors takes into account, that the effect of the isocenter to monitor correction may not be constant between the reference layer measurement and the layer i. This term is very close to 1 for a typical beam-line design, where the dose monitor is at an end of the beam-line, except if the range of the beam is of similar magnitude as the NeT. The range of the beam and NeT are considered similar, if the range of the beam is not larger than NeT by more than 5-6 cm for typical values of IsoMonWeT of 2-3 mm. The dose of a low energy Bragg peak increases quickly after the monitor chamber under these circumstances. Therefore, this correction may be desirable.

The range shift between monitor chamber and isocenter is an estimated value, which can also be used for fine-tuning. The range shift between monitor and isocenter is typically caused by air and the exit window of the monitor. It is in the order of 2 mm, but may have other values in other embodiments.

Note that the equation above can also be used to predict the MU factor, if NeT is kept constant and the nominal energy varies. For example, in some embodiments, it may be desirable to replace the entrance dose ratio as a function of NeT differences, by the entrance dose ratio as a function of energy changes. In some cases, the last two terms may be dropped out to simplify the calculation.

In other embodiments, the MU factors may be obtained without using all of the above correction factors. For example, in other embodiments, any one or two of the last three terms may be omitted in the above equation. Also, in other embodiments, additional correction factors that account for other contributing factors that cause variation of Bragg peaks may be applied to calculate the MU factors.

Next, different MU factors associated with different layers are combined to determine MU (Step 808). For example, the MU factors may be summed together. In some embodiments, different weight factors are applied respectively to the MU factors for different layers, and the weighted MU factors are then summed together to determine the MU. The weight factors may be obtained by a numerical optimization process in order to achieve a desired (e.g., flat) SOBP. In some cases, it is also possible to explicitly choose a non-flat SOBP shape (e.g. to boost the inner part of the target) and optimize the weights to that shape.

As illustrated, the MU factors for respective Bragg peaks (due to beam going through different absorbing material in the beam-line) are obtained by using the normalization factor, correcting for intensity changes as taken from the fluence measurements, and by correcting for the effect of a different position of the monitor chamber in relation to the shape of the Bragg curve. As illustrated in the above embodiments, such MU calculation method is advantageous in that it does not require measurement of a large set of SOBPs, i.e., different combinations of ranges and modulation. This is because the MU calculation is based on Bragg peak measurements. The above technique is applicable to different types of proton irradiation techniques, such as scattering or scanning (uniform scanning, raster scanning, and wobbling). The above method also allows one to predict accurately the MUs for a variety of treatment situations. Furthermore, the above method does not require a lot of calibration measurements to find machine specific factors, such as properties of the incoming beam and scattering behavior of the beamline elements, and is independent of the details of the treatment machine. Note that the above technique involves one calibration measurement per energy at nozzle entrance, as opposed to one per combination of range (energy) and SOBP width.

Also, as illustrated in the above embodiments, the above method allows one to predict MUs for individual layers of Bragg peaks for layer based application techniques. The definition of layer MUs for these techniques was previously a trial and error approach. In further embodiments, the above method can also be used to design range modulators with the appropriate relative weights of the range modulator steps.

In still further embodiments, in the layer based application technique, the above method allows one to prescribe non-flat SOBPs, e.g., for an integrated boost to a sub-volume of the target. For example, a target area may include a tumor and a surrounding area next to the tumor (margin) to account for possible microscopic spread of tumor cells. The dose to be delivered to the solid tumor may be desired to be higher than the dose to the margin. Conventionally, this is achieved by two separate treatment plans, one for the whole target area and one only for the solid tumor. The embodiments of the technique described herein provide accurate prediction of the layer MUs, thereby allowing a desired dose to be delivered to the tumor and the margin in a single delivery.

Field Specific MU or Absolute Dose Calculation

The MU factors (as a function of energy and NeT) can be determined universally for any given machine. In some cases, different prerequisites may be prescribed for calculating MU for a particular field. For examples, the following prerequisites may be used:

(1) No dose nor MU prescription: In this case, the system calculates a set of MUs and matching absolute dose distribution. In particular, the system calculates the ratio between the dose in any point in the patient and the monitor units. The user may select either a prescription dose or the delivered monitor units. The system then updates the required MUs or absolute dose distribution, respectively. In this use case, the system implicitly assumes a flat dose distribution in the target and optimizes the layer weights.

(2) Total MUs and/or layer MUs are prescribed: In this case, the system calculates the absolute dose distribution. The field has already been applied to either a patient or a water phantom. The user enters the MUs and finds the delivered dose.

(3) Relative weights of the layers is prescribed: In this case, the system calculates a valid combination of the absolute dose distribution and the total MUs.

(4) The dose to a point is prescribed: In this case, the system calculates the MUs to deliver the required dose at a point, and the whole 3D dose distribution. In particular, the dose to one point in the target is defined by the physician. The system assumes a uniform prescribed dose throughout the target. It optimizes the relative layer weights in order to create a flat SOBP, and then calculates the layer MUs and total MUs to give the desired dose.

Although, the actual work-flow for the MU/absolute dose calculation may vary from case to case, the following approach may always be used. The depth dose of individual Bragg peaks is calculated as a function of the nominal energy and energy spectrum. It is not possible to produce a beam where all protons have exactly the same energy. There is always some broader distribution of the energy of the individual protons. This distribution is the energy spectrum. In the analytical algorithm, one can get the depth dose curve in units of MeV/cm (per proton). Applying the MU factor, such depth dose curve can be converted to a depth dose curve in units of Gy/MU for an individual Bragg peak. If it is desirable to calculate the MUs to be delivered for an SOBP of predefined modulation and plateau dose, then MUs for the individual layers are optimized to reach a plateau with the given dose. The sum of the layer MUs corresponds to the total MUs for the desired SOBP. This approach works for scattering techniques as well as for uniform scanning techniques, where layers are typically applied sequentially. This approach may also be applied to individual pencil beams in the modulated scanning technique. Depending on the application, it may also be desirable to calculate a beamlet (e.g., a 3D distribution) of dose in Gy/MU by taking the lateral distribution into account.

As illustrated in the above embodiments, each MU factor is a function of NeT. Each MU factor may also be a function of energy E. For example, in other embodiments, the above method may be performed repeatedly for different energies. As a result, a surface in a three dimensional space may be created in which one axis represents energy, another axis represents NeT, and a third axis represents MU factors. In some cases, if the energy is kept constant per field, such surface may be used to obtain MU factors for different NeTs. In other cases, if the NeT per layer is kept constant, then the energy may be varied instead, and the three-dimensional surface may be used to obtain MU factors for different energies.

Although the above embodiments have been described with reference to monitor units for proton fields, the above method may also be used to determine monitor units for other types of ions.

Computer System Architecture

Figure 10:
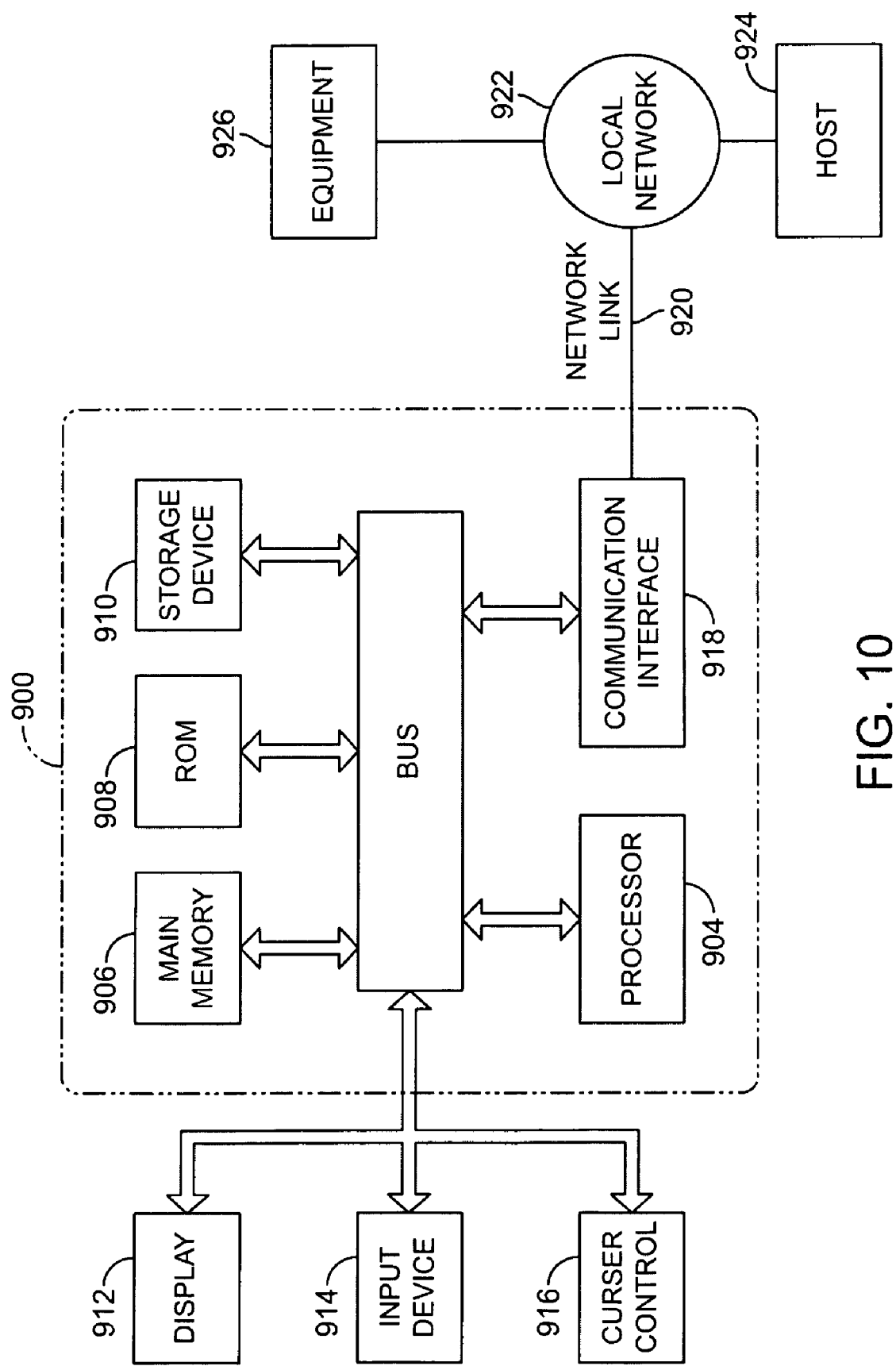
FIG. 10 is a block diagram of a computer system architecture, with which embodiments described herein may be implemented.

FIG. 10 is a block diagram that illustrates an embodiment of a computer system 900 upon which an embodiment of the invention may be implemented. Computer system 900 includes a bus 902 or other communication mechanism for communicating information, and a processor 904 coupled with the bus 902 for processing information. The processor 904 may be an example of the processor 54 of FIG. 1, or another processor that is used to perform various functions described herein. In some cases, the computer system 900 may be used to implement the processor 54. The computer system 900 also includes a main memory 906, such as a random access memory (RAM) or other dynamic storage device, coupled to the bus 902 for storing information and instructions to be executed by the processor 904. The main memory 906 also may be used for storing temporary variables or other intermediate information during execution of instructions to be executed by the processor 904. The computer system 900 further includes a read only memory (ROM) 908 or other static storage device coupled to the bus 902 for storing static information and instructions for the processor 904. A data storage device 910, such as a magnetic disk or optical disk, is provided and coupled to the bus 902 for storing information and instructions.

The computer system 900 may be coupled via the bus 902 to a display 912, such as a cathode ray tube (CRT), for displaying information to a user. An input device 914, including alphanumeric and other keys, is coupled to the bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane.

The computer system 900 may be used for performing various functions (e.g., calculation) in accordance with the embodiments described herein. According to one embodiment, such use is provided by computer system 900 in response to processor 904 executing one or more sequences of one or more instructions contained in the main memory 906. Such instructions may be read into the main memory 906 from another computer-readable medium, such as storage device 910. Execution of the sequences of instructions contained in the main memory 906 causes the processor 904 to perform the process steps described herein. One or more processors in a multi-processing arrangement may also be employed to execute the sequences of instructions contained in the main memory 906. In alternative embodiments, hardwired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 904 for execution. Such a medium may take many forms, including but not limited to, non-volatile media, volatile media, and transmission media. Non-volatile media includes, for example, optical or magnetic disks, such as the storage device 910. Volatile media includes dynamic memory, such as the main memory 906. Transmission media includes coaxial cables, copper wire and fiber optics, including the wires that comprise the bus 902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 904 for execution. For example, the instructions may initially be carried on a magnetic disk of a remote computer. The remote computer can load the instructions into its dynamic memory and send the instructions over a telephone line using a modem. A modem local to the computer system 900 can receive the data on the telephone line and use an infrared transmitter to convert the data to an infrared signal. An infrared detector coupled to the bus 902 can receive the data carried in the infrared signal and place the data on the bus 902. The bus 902 carries the data to the main memory 906, from which the processor 904 retrieves and executes the instructions. The instructions received by the main memory 906 may optionally be stored on the storage device 910 either before or after execution by the processor 904.

The computer system 900 also includes a communication interface 918 coupled to the bus 902. The communication interface 918 provides a two-way data communication coupling to a network link 920 that is connected to a local network 922. For example, the communication interface 918 may be an integrated services digital network (ISDN) card or a modem to provide a data communication connection to a corresponding type of telephone line. As another example, the communication interface 918 may be a local area network (LAN) card to provide a data communication connection to a compatible LAN. Wireless links may also be implemented. In any such implementation, the communication interface 918 sends and receives electrical, electromagnetic or optical signals that carry data streams representing various types of information.

The network link 920 typically provides data communication through one or more networks to other devices. For example, the network link 920 may provide a connection through local network 922 to a host computer 924 or to equipment 926 such as a radiation beam source or a switch operatively coupled to a radiation beam source. The data streams transported over the network link 920 can comprise electrical, electromagnetic or optical signals. The signals through the various networks and the signals on the network link 920 and through the communication interface 918, which carry data to and from the computer system 900, are exemplary forms of carrier waves transporting the information. The computer system 900 can send messages and receive data, including program code, through the network(s), the network link 920, and the communication interface 918.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method for determining a monitor unit that is associated with a process using ions, comprising:
    obtaining a depth dose curve;
    determining a characteristic parameter based on the depth dose curve;
    using the characteristic parameter to determine a first monitor unit factor for a first layer that is associated with a first feature of a range modulator; and
    storing the first monitor unit factor in a device having a non-transitory medium;
    wherein the act of using the characteristic parameter to determine the first monitor unit factor is performed by a processor.

2. The method of claim 1, wherein the depth dose curve is obtained by measurement.

3. The method of claim 1, wherein the depth dose curve is a model.

4. The method of claim 3, further comprising fitting the model to a measured depth dose curve.

5. The method of claim 1, further comprising applying a correction factor to the characteristic parameter.

6. The method of claim 5, wherein the correction factor is based on an entrance dose.

7. The method of claim 5, wherein the correction factor is a ratio of an entrance dose for a nozzle equivalent thickness associated with a layer, to an entrance dose for a reference nozzle equivalent thickness.

8. The method of claim 5, wherein the correction factor is based on a fluence at an isocenter.

9. The method of claim 5, wherein the correction factor is a ratio of a fluence at isocenter for a reference nozzle equivalent thickness, to a fluence at isocenter for a nozzle equivalent thickness associated with a layer.

10. The method of claim 5, wherein the correction factor is a function of entrance dose, fluence at isocenter, nozzle equivalent thickness associated with a layer, and a reference nozzle equivalent thickness.

11. The method of claim 5, wherein the correction factor is a correction for a ratio of values of an entrance dose at a monitor position and at an isocenter.

12. The method of claim 1, further comprising:
    obtaining a second monitor unit factor for a second layer that is associated with a second feature of the range modulator; and
    combining the first and second monitor unit factors to obtain a monitor unit.

13. The method of claim 12, wherein the monitor unit is obtained by:
    applying a first weighted factor to the first monitor unit factor to obtain a first weighted monitor unit factor;
    applying a second weighted factor to the second monitor unit factor to obtain a second weighted monitor unit factor; and
    summing the first and second weighted monitor unit factors.

14. The method of claim 1, wherein the ions comprise protons.

15. A system for determining a monitor unit that is associated with a process using ions, the system comprising a processor, wherein the processor is configured for:
    obtaining a depth dose curve;
    determining a characteristic parameter based on the depth dose curve; and
    using the characteristic parameter to determine a first monitor unit factor for a first layer that is associated with a first feature of a range modulator.

16. The system of claim 15, wherein the depth dose curve is obtained by measurement.

17. The system of claim 15, wherein the depth dose curve is a model.

18. The system of claim 17, wherein the processor is further configured for fitting the model to a measured depth dose curve.

19. The system of claim 15, wherein the characteristic parameter comprises a normalization factor.

20. The system of claim 19, wherein the normalization factor is for converting a unit of dose in a model into another unit of dose.

21. The system of claim 15, further comprising applying a correction factor to the characteristic parameter.

22. The system of claim 21, wherein the correction factor is based on an entrance dose.

23. The system of claim 21, wherein the correction factor is a ratio of an entrance dose for a nozzle equivalent thickness associated with a layer, to an entrance dose for a reference nozzle equivalent thickness.

24. The system of claim 21, wherein the correction factor is based on a fluence at an isocenter.

25. The system of claim 21, wherein the correction factor is a ratio of a fluence at isocenter for a reference nozzle equivalent thickness, to a fluence at isocenter for a nozzle equivalent thickness associated with a layer.

26. The system of claim 21, wherein the correction factor is a function of entrance dose, fluence at isocenter, nozzle equivalent thickness associated with a layer, and a reference nozzle equivalent thickness.

27. The system of claim 21, wherein the correction factor is a correction for a ratio of values of an entrance dose at a monitor position and at an isocenter.

28. The system of claim 15, wherein the processor is further configured for: further comprising:
   obtaining a second monitor unit factor for a second layer that is associated with a second feature of the range modulator; and
   combining the first and second monitor unit factors to obtain a monitor unit.

29. The system of claim 28, wherein the processor is configured to obtain the monitor unit by:
   applying a first weighted factor to the first monitor unit factor to obtain a first weighted monitor unit factor;
   applying a second weighted factor to the second monitor unit factor to obtain a second weighted monitor unit factor; and
   summing the first and second weighted monitor unit factors.

30. The system of claim 15, wherein the ions comprise protons.

31. A computer product having a set of instructions stored in a non-transitory medium, an execution of which causes a process to be performed, wherein the process is for determining a monitor unit that is associated with a process using ions, the process comprising:
   obtaining a depth dose curve;
   determining a characteristic parameter based on the depth dose curve; and
   using the characteristic parameter to determine a first monitor unit factor for a first layer that is associated with a first feature of a range modulator.

32. The computer product of claim 31, wherein the process further comprises:
   obtaining a second monitor unit factor for a second layer that is associated with a second feature of the range modulator; and
   combining the first and second monitor unit factors to obtain a monitor unit.

33. The computer product of claim 32, the first and second features comprise a first thickness and a second thickness, respectively, of the range modulator.

34. The computer product of claim 31, wherein the range modulator is for reducing an energy of a beam, and has a step configuration.

35. The method of claim 1, wherein the range modulator is for reducing an energy of a beam, and has a step configuration.

36. The method of claim 12, wherein the first and second features comprise a first thickness and a second thickness, respectively, of the range modulator.

37. The system of claim 15, wherein the range modulator is for reducing an energy of a beam, and has a step configuration.

38. The system of claim 28, wherein the first and second features comprise a first thickness and a second thickness, respectively, of the range modulator.

* * * * *